United States Patent [19]
Yamamoto et al.

[11] Patent Number: 6,031,127
[45] Date of Patent: Feb. 29, 2000

[54] PROCESS FOR PREPARING L-P-BORONOPHENYLALANINE AND INTERMEDIATE FOR PREPARING THE SAME

[75] Inventors: Yoshinori Yamamoto; Hiroyuki Nakamura; Masaru Fujiwara, all of Sendai, Japan

[73] Assignee: Tohoku University, Miyagi Pref., Japan

[21] Appl. No.: 09/218,190

[22] Filed: Dec. 22, 1998

[30] Foreign Application Priority Data

Mar. 11, 1998 [JP] Japan ................................. 10-059346

[51] Int. Cl.[7] .................................................. C07C 229/28
[52] U.S. Cl. ................................ 562/443; 549/213; 568/6
[58] Field of Search ................................ 568/6; 549/213; 562/443

[56] References Cited

PUBLICATIONS

Synlett, 1996, p167–168, Malan et al., 'Synthesis of 4–Borono–L–phenylalanine.'

J. Org. Chem. 1995, 60, p7508–7510, Ishiyama et al., 'Palladium(O)–Catalyzed Cross–Coupling Reaction of Alkoxydiboron with Haloarenes: A Direct Proceedure for Arylboronic Esters.',1995.

*Primary Examiner*—Gary Geist
*Assistant Examiner*—Brian J. Davis
*Attorney, Agent, or Firm*—Knobbe, Martens, Olson & Bear, LLP.

[57] ABSTRACT

There is disclosed a process for preparing L-p-boronophenylalanine which comprises subjecting a compound represented by the formula:

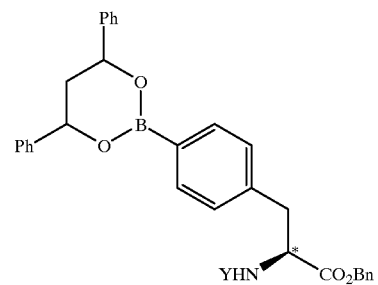

wherein Y represents a protective group selected from the group consisting of benzyloxycarbonyl group, allyloxycarbonyl group and t-butoxycarbonyl group; and Bn represents benzyl group, to hydrogenation reaction in the presence of a palladium series catalyst, and a synthetic intermediate represented by the above formula for preparing the same.

6 Claims, No Drawings

PROCESS FOR PREPARING L-P-BORONOPHENYLALANINE AND INTERMEDIATE FOR PREPARING THE SAME

BACKGROUND OF THE INVENTION

1. Field of the Invention

This invention relates to a process for preparing L-p-boronophenylalanine and an intermediate for preparing the same.

2. Prior Art

As a cancer treating method, a so-called neutron capturing method has been clinically employed only in Japan, but in recent years, it is now clinically applying also in the United States, Europe and Australia. Medicines which are now clinically applied are only BSH and L-p-boronophenylalanine. It is the sole medicine for treatment used not only for a skin cancer but also a cerebral tumor well taken therein, and has now been supplied from BBI Co. of U.S.A. It has now been synthesized by the method as shown below.

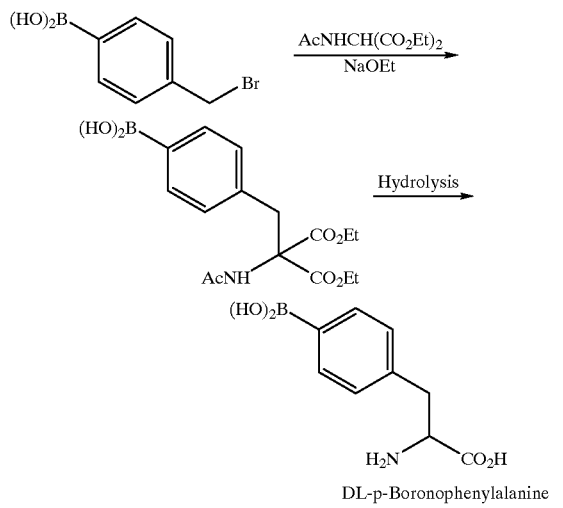

In this synthetic method, DL-isomers (racemic isomers) of p-boronophenylalanine are obtained (see H. R. Synder, A. J. Reedy and W. M. J. Lennarz, "J. Am. Chem. Soc." (1958), vol. 80, p.835) so that it is necessary to finally separate and purify the L-isomer by an optical resolution. Thus, the method is high in cost and a patient must pay the expenses for one treatment with several ten thousand dollars.

To solve the above problems, the following selective synthetic method of an optically active L-p-boronophenylalanine has been developed in recent years.

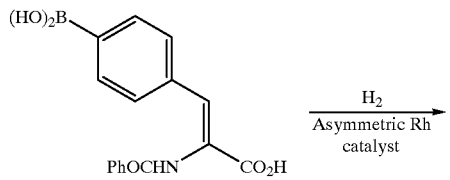

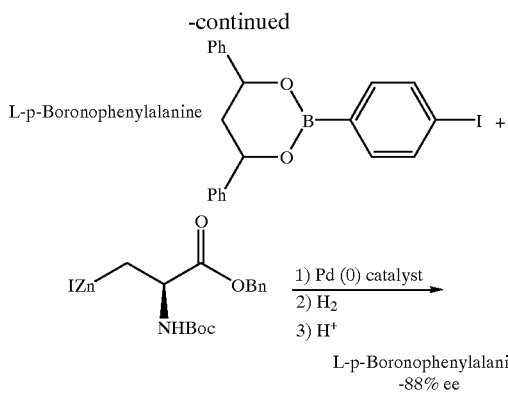

In the above-mentioned asymmetrically reducing method using a rhodium catalyst, an asymmetric yield is atmost 88% and requires to finally separate and purify the L-isomer (see E. G. Samsel, U.S. Pat. No. 5,157,149, 1992). Also, in the above method deriving from L-serine, there involves the problem that an yield of the coupling reaction with aryl iodide is low as 50 to 55% (see C. Malan and C. Morin, "SYNLETT", 1996, p.167).

SUMMARY OF THE INVENTION

An object of the present invention is to provide a novel process for synthesizing L-para-boronophenylalanine without separating the L- and D-optical isomers at the final stage.

Another object of the present invention is to reduce an expense which costs for separation and purification, by using a cheap compound as a starting material and removing the separation and purification processes of an optical isomer.

Still further object of the present invention is to establish a convergent type synthetic method which does not dispose any unnecessary waste metals and does not damage the natural environment.

The present invention is a process for preparing L-p-boronophenylalanine represented by the following formula:

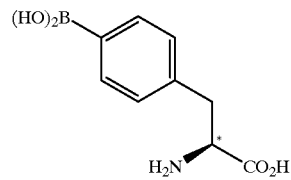

which comprisis subjecting a compound represented by the formula:

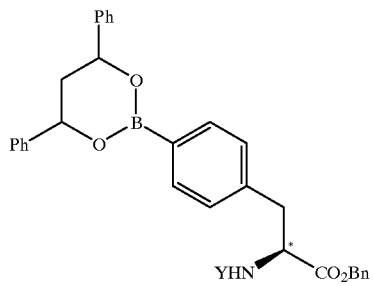

wherein Y represents a protective group selected from the group consisting of benzyloxycarbonyl group, allyloxycarbonyl group and t-butoxycarbonyl group; and Bn represents benzyl group,
to hydrogenation reaction in the presence of a palladium series catalyst.

An intermediate for preparing L-p-boronophenyl-alanine of the present invention is a compound represented by the formula:

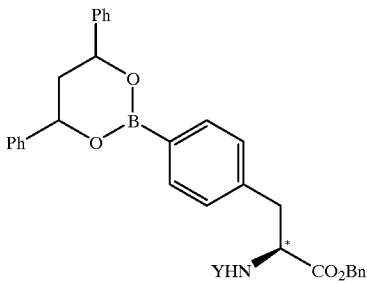

wherein Y and Bn have the same meanings as defined above.

DESCRIPTION OF THE PREFERRED EMBODIMENTS

As the palladium series catalyst to be used for the hydrogenation reaction, all the catalysts effectively catalyzes the reaction may be used, including palladium hydroxide, palladium black and palladium carried on an active charcoal, particularly preferably palladium hydroxide. As the solvent to be used in the hydrogenation reaction, there may be mentioned, for example, ethyl acetate, chloroform, methanol, ethanol, dichloromethane, tetrahydrofuran. The hydrogenation reaction can be carried out at the temperature of, for example, room temperature to 40° C.

In the preparation process of the present invention, the starting compound of the following formula:

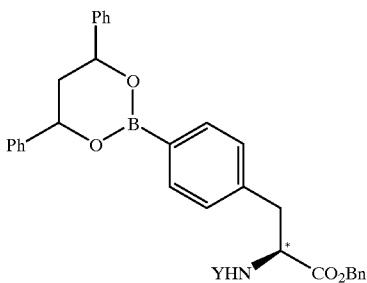

wherein Y and Bn have the same meanings as defined above, can be prepared by obtaining a triflate derivative represented by the following formula:

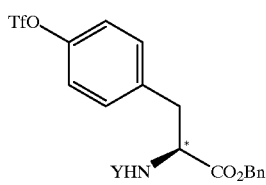

wherein Tf represents trifluoromethanesulfonyl group; and Y and Bn have the same meanings as defined above, which is prepared preferably from N-t-butoxycarbonyl-L-tyrosine, N-allyloxycarbonyl-L-tyrosine or N-benzyloxycarbonyl-L-tyrosine, then, reacting the triflate derivative with tetraalkoxydiboron represented by the following formula:

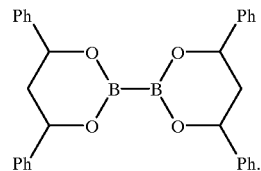

N-benzyloxycarbonyl-L-tyrosine is commercially available or can be synthesized from L-tyrosine according to the conventionally known method. N-allyloxycarbonyl-L-tyrosine or N-t-butoxycarbonyl-L-thyrosine can be synthesized from L-tyrosine according to the conventionally known method. For synthesizing the above-mentioned triflate derivative from N-benzyloxycarbonyl-L-thyrosine, N-allyloxycarbonyl-L-thyrosine or N-t-butoxycarbonyl-L-thyrosine, the reaction can be carried out by firstly reacting the above starting compound with benzyl bromide in the presence of $CsCO_3$ to subject the carboxyl group to benzylesterification, then reacting the resulting compound with $TfO_2$ (see W. Wang, N. U. Obeyesekere, J. S. McMurray, "Tetrahedron Letters", 1996, 37, 6661).

The above-mentioned tetraalkoxydiboron can be obtained by reacting a diboron with a propanediol compound. Also, the coupling reaction of the above-mentioned triflate derivative and tetraalkoxydiboron can proceed in the presence of a palladium series catalyst. As the palladium series catalyst, there may be mentioned, for example, palladium chloride, π-allylpalladium chloride, palladium tetrakistriphenylphosphine, dichloro (bis-diphenylphosphinoferrocene) palladium and particularly preferably palladium chloride. As the solvent to be used in the above reaction, there may be mentioned, for example, dimethylformamide, tetrahydrofuran, dimethylsulfoxide, etc. The reaction can be carried out at a temperature of, for example, 80° C. to 100° C.

By using the above-mentioned preparation method and the intermediate, the present inventors have succeeded in asymmetrically synthesizing L-p-boronophenylalanine from a low cost L-tyrosine with a high yield.

In the conventional boron-introducing reaction, ionic and strong basic conditions are required so that the method is difficult to apply to a compound having a highly reactive functional group (for example, a functional group essential for a living body-related substance such as an amino acid, a carbonyl group, a carboxyl group, etc.). As the results, in the course of synthesizing a compound, a boron atom is firstly introduced, then the skeleton of the compound is constituted and a functional group is introduced so that racemization of a chiral compound or stereospecific control of the reaction cite caused problems. Thus, the resulting reaction mixture must be finally separated and purified.

In the present invention, starting from a hydroxyl group of a substrate, a boron atom can be introduced into the position of the hydroxyl group. Thus, the reaction can be carried out under extremely mild reaction conditions, by using a palladium series catalyst, which is quite different from the conventional ionic reaction. As the results, it is possible to apply the reaction to a compound having a functional group with a high reactivity (for example, a functional group essential for a living body-related substance such as an amino acid, a carbonyl group, a carboxyl group, etc.).

Moreover, the catalytic reaction of the present invention is different from the conventional stoichiometric reaction in that it is a convergent type synthetic method, which does not dispose any unnecessary waste metals and does not damage the natural environment.

EXAMPLES

In the following, the present invention is explained in more detail by referring to specific examples.

The following triflate derivative 1 was obtained according to the method described in W. Wang, N. U. Obeyesekere, J. S. McMurray, "Tetrahedron Letters", 1996, 37, 6661, by using a low-cost commercially-available L-tyrosine as a starting material. In the formula, Z represents a benzyloxycarbonyl group. Physicochemical properties of the triflate derivative 1 are shown below.

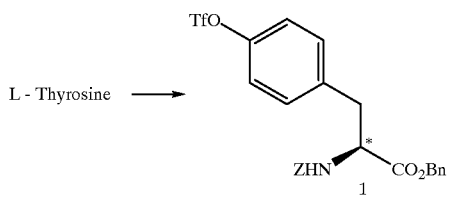

$^1$H NMR (CDCl$_3$) δ 7.32 (s, 9H), 7.02 (s, 5H), 5.25 (d, J=8.0 Hz, 1H), 5.07 (s, 4H), 4.68 (m, 1H), 3.14 (dd, J=13.2, 5.6 Hz, 1H) 3.05 (dd, J=13.2, 5.6 Hz, 1H).
$^{13}$C NMR (CDCl$_3$) δ 170.74, 155.38, 148.44, 136.20, 135.97, 134.69, 131.09, 128.79, 128.73, 128.66, 128.51, 128.27, 128.14, 121.24, 120.99, 67.53, 67.11, 54.55, 37.40.
[a]$_D$20.9° C.+2.87° (c=1.055, CHCl$_3$).

Diboron 2 was reacted with propane diols 3a and 3b as mentioned in the following reaction scheme to synthesize tetraalkoxydiborons 4a and 4b, respectively.

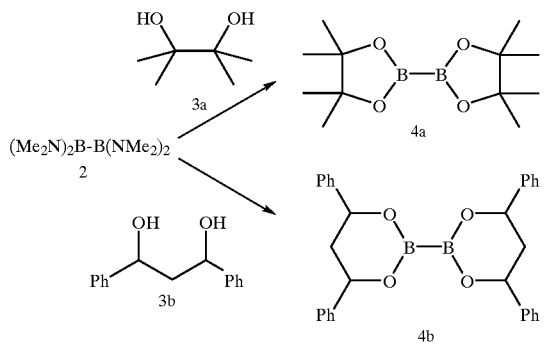

Synthetic Example of Tetraalkoxydiboron 4b is Mentioned Below.

Diboron 2 (3.16 g, 16.0 mmol) was dissolved in tetrahydrofuran (40 ml), and to the solution was added dropwise a tetrahydrofuran (40 ml) solution containing 1,3-diphenyl-1, 3-propanediol 3b (7.3 g, 32 mmol) gradually at room temperature. The mixture was stirred at 50° C. over a whole day and night and the solvent was removed under reduced pressure. The resulting crude product was reprecipitated from tetrahydrofuran to give the compound 4b (white solid, 5.43 g, yield: 72%). Physicochemical properties of the resulting compound are shown below.
$^1$H NMR (CDCl$_3$) δ 7.34 (m, 20H), 5.08 (t, J=5.3 Hz, 4H), 2.36 (dd, J=5.3, 5.3 Hz, 4H).

$^{13}$C NMR (CDCl$_3$) δ 141.94, 128.40, 127.36, 125.18, 69.77, 41.84.

When the triflate derivative 1 was reacted with tetraalkoxydiboron 4 (4a or 4b) in the presence of a palladium series catalyst, coupling reaction proceeds to give an arylborate 5 (5a or 5b) with a high yield.

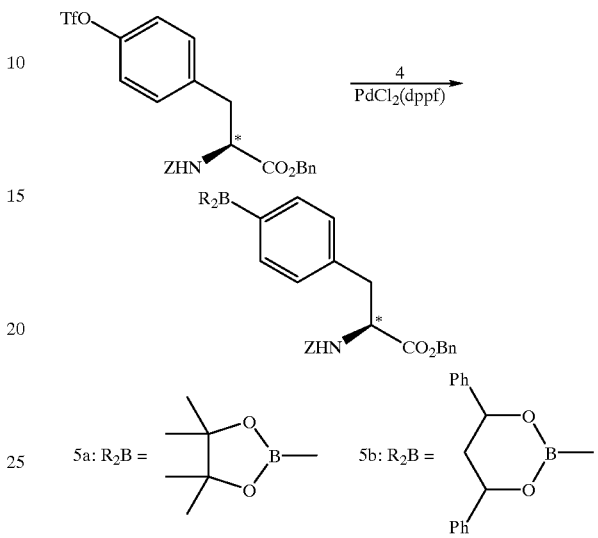

In the tetraalkoxydiboron 4a derived from pinacol, the reaction was completed in dioxane at 80° C. for 5 hours to give an arylborate 5a quantitatively (T. Ishiyama, M. Murata, N. Miyaura, "J. Org. Chem." 1995, 60, 7508–7510). Also, in the tetraalkoxydiboron 4b derived from 1,3-diphenyl-1,3-propanediol 3b, the reaction was completed in dimethylformamide at 100° C. for 3 hours to give an arylborate 5b with a yield of 65%.

In the following, synthetic example of Compound 5b is described.

In dimethylformamide (20 ml) were dissolved the triflate derivative 1 (1.34 g, 2.49 mmol), bis(1,3-diphenyl-1,3-propanediolate) diboron 4b (1.30 g, 2.74 mmol), potassium acetate (0.73 g, 7.48 mmol), dichloro(bis-diphenylphosphino-ferrocene) palladium (0.15 g, 0.20 mmol), and the mixture was stirred at 100° C. for 3 hours. The reaction mixture was cooled to room temperature, diluted with ethyl acetate and washed with a saturated saline solution. The organic layer was dried over anhydrous magnesium sulfate, the solvent was removed under reduced pressure and the resulting crude product was purified by silica gel column chromatography (hexane/ethyl acetate=6/1) to give the compound 5b (white solid, 1.04 g, yield: 65%). Physicochemical properties of the resulting compound are shown below.
$^1$H NMR (CDCl$_3$) δ 7.86 (d, J=7.3 Hz, 2H), 7.36 (m, 20H), 7.08 (d, J=7.3 Hz, 2H), 5.25 (m, 1H), 5.21 (t, J=5.2 Hz, 2H), 5.15 (s, 2H), 5.10 (s, 2H), 4.75 (m, 1H), 3.15 (bs, 2H), 2.40 (dd, J=5.2, 5.2 Hz, 2H).

In the case of the arylborate 5a, in acetone solution containing sodium periodate and ammonium acetate for deprotecting pinacol, racemization was observed.

Thus, by using the arylborate 5b, when all the protective groups are tried to be removed by effecting hydrogenation in the presence of palladium hydroxide catalyst, the desired compound L-p-boronophenylalanine (L-BPA) was obtained with a yield of 74% without racemization as mentioned below.

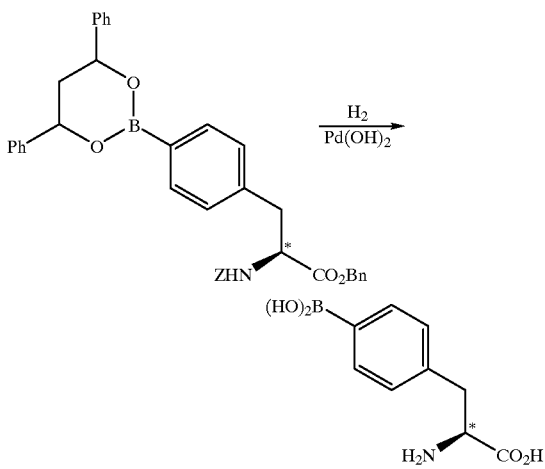

That is, the arylborate 5b (0.38 g, 0.59 mmol) was dissolved in a mixed solvent of ethyl acetate (5 ml), chloroform (5 ml) and methanol (5 ml), and after adding palladium hydroxide (0.10 g), one drop of acetic acid was added to effect hydrogen substitution and the mixture was stirred at 40° C. for 24 hours. Palladium catalyst was removed by filtration through celite. To the reaction mixture was added 1 ml of water, the solvent was removed washed with methylene chloride to give L-p-boronophenylalanine (0.09 g, yield: 74%).

What is claimed is:

1. A process for preparing L-P-boronophenylalanine of the following formula:

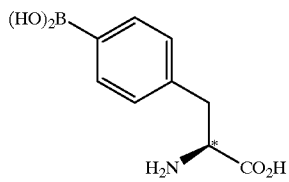

said process comprising the steps of:
preparing a triflate compound represented by the following formula:

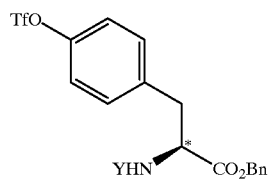

wherein Tf represents trifluoromethanesulfonly group; and Y is a protective group selected from the group consisting of benzyloxycarbonyl group, allyloxycarbonyl group, and t-butoxycarbonyl group; and Bn is an benzyl group, from a starting material selected from the group consisting of N-t-butoxycarbonyl-L-thyrosine, N-allyloxycarbonyl-L-thyrosine and N-benzyloxycarbonyl-L-thyrosine, reacting the triflate compound with tetraalkoxydiboron represented by the following formula:

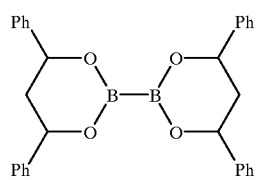

to obtain a compound of the formula:

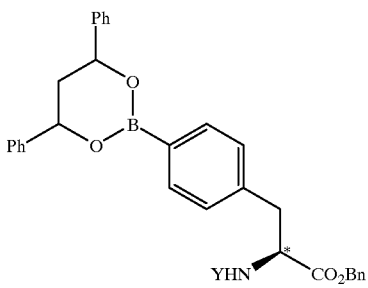

wherein Y and Bn are as defined above, and
subjecting said compound to hydrogenation reaction in the presence of a palladium series catalyst.

2. The process according to claim 1, wherein said palladium series catalyst is selected from the group consisting of palladium hydroxide, palladium black, and palladium carried on an active charcoal.

3. The process according to claim 1, wherein said triflate compound is reacted with said tetraalkoxydiboron in the presence of a palladium series catalyst.

4. The process according to claim 3, wherein said palladium series catalyst is selected from the group consisting of palladium chloride, π-allylpalladium chloride, palladium tetrakistriphenylphosphine, and dichloro(bis-diphenylphosphinoferrocene)palladium.

5. The process according to claim 1, wherein said protective group is benzyloxycarbonyl group, and said starting material is N-benzyloxycarbonyl-L-thyrosine.

6. The process according to claim 3, wherein said protective group is benzyloxycarbonyl group, and said starting material is N-benzyloxycarbonyl-L-thyrosine.

* * * * *